US008057520B2

(12) United States Patent
Ducharme et al.

(10) Patent No.: US 8,057,520 B2
(45) Date of Patent: Nov. 15, 2011

(54) CALCANEAL PLATE

(75) Inventors: Dustin Ducharme, Stow, OH (US);
Bryan D. Den Hartog, Rapid City, SD (US); Michael C. McGlamry, Marietta, GA (US); Bharat M. Desai, Golden, CO (US); David B. Kay, Akron, OH (US); Lee A. Strnad, Broadview Hts., OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 1122 days.

(21) Appl. No.: 11/879,118

(22) Filed: Jul. 16, 2007

(65) Prior Publication Data
US 2008/0021452 A1 Jan. 24, 2008

Related U.S. Application Data

(60) Provisional application No. 60/831,647, filed on Jul. 18, 2006, provisional application No. 60/880,910, filed on Jan. 17, 2007.

(51) Int. Cl.
*A61B 17/80* (2006.01)

(52) U.S. Cl. ...................................................... 606/280

(58) Field of Classification Search ........... 606/280–297
See application file for complete search history.

(56) References Cited

U.S. PATENT DOCUMENTS

| | | | | |
|---|---|---|---|---|
| 4,503,848 A | * | 3/1985 | Caspar et al. | 606/280 |
| 4,905,680 A | * | 3/1990 | Tunc | 606/280 |
| 5,690,631 A | * | 11/1997 | Duncan et al. | 606/281 |
| 6,123,709 A | * | 9/2000 | Jones | 606/281 |
| 6,235,032 B1 | | 5/2001 | Link | |
| 7,179,260 B2 | * | 2/2007 | Gerlach et al. | 606/291 |
| 7,731,718 B2 | * | 6/2010 | Schwammberger et al. | 606/71 |
| 2004/0167522 A1 | | 8/2004 | Niederberger et al. | |
| 2004/0210220 A1 | | 10/2004 | Tornier | |
| 2005/0070904 A1 | | 3/2005 | Gerlach et al. | |
| 2006/0259039 A1 | | 11/2006 | Pitkanen et al. | |

OTHER PUBLICATIONS

New Trauma Products from AO Development, Jun. 2006 (pp. 2&3).
Foot Reconstructive and Trauma Surgery—Internal and External Fixation Systems May 29, 2008 (pp. 2-12).
New Trauma Products from AO Development, Jun. 2006 (pp. 1-8).
A Straight Answer for Kids, Jan. 2007 (4 pages).

* cited by examiner

*Primary Examiner* — Thomas C. Barrett
*Assistant Examiner* — Michael Araj
(74) *Attorney, Agent, or Firm* — Hudak, Shunk & Farine Co. LPA

(57) ABSTRACT

The present invention is a fully contoured calcaneal plate having substantially no planar surfaces except at the origin. The contoured plate includes radiused sections, one extending inferior to superior is curved inferior to superior in a shape which is close to cylindrical and which approximates the shape of the cuboid bone. The second radiused section is curved in the vicinity of the anterior strut, and in particular at the inferior portion of the plate, to accommodate the peroneal tubercle. The plate has a rectangular or modified ovoid body section and a dog boned shaped tail with triangular placed holes for fixation.

29 Claims, 3 Drawing Sheets

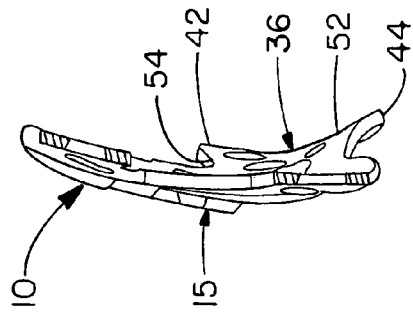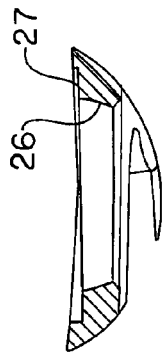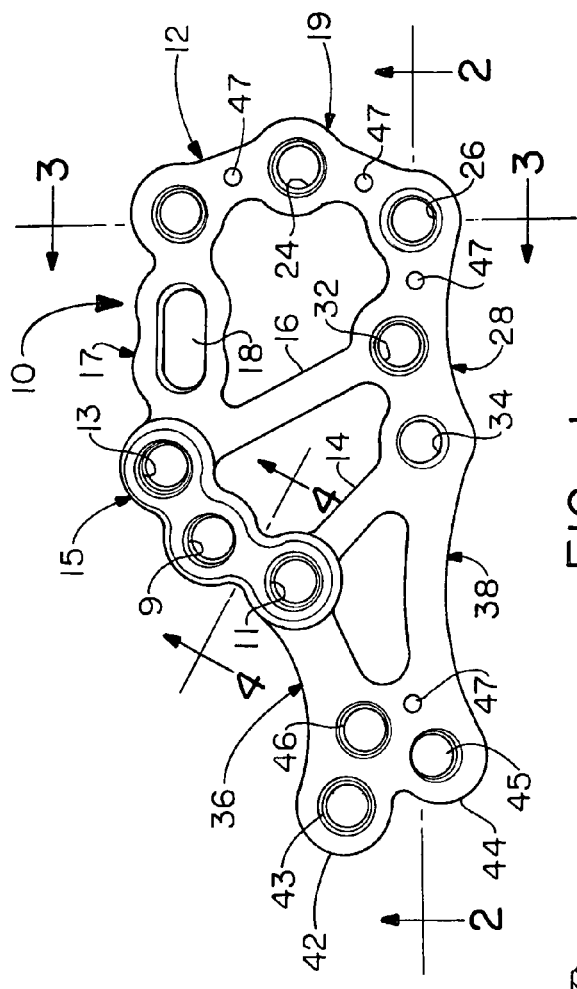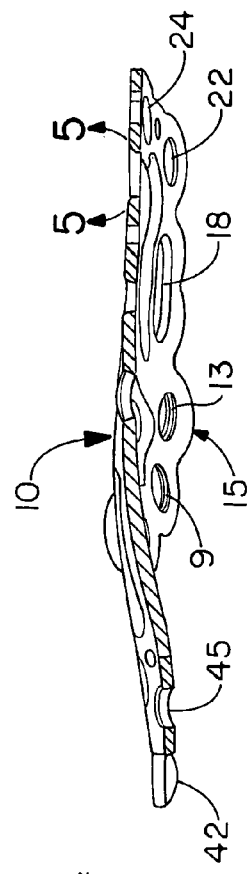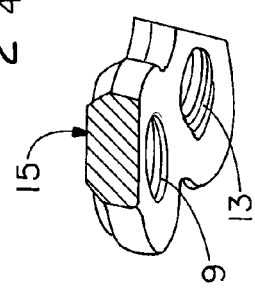

CALCANEAL PLATE

This Patent application claims priority to U.S. Provisional applications Nos. 60/831,647, filed Jul. 18, 2006 for CALCANEAL PLATE and 60/880,910, filed Jan. 17, 2007 for CALCANEAL PLATE which is hereby fully incorporated by reference

THE FIELD OF THE INVENTION

The present invention relates to an orthopedic implant for use in fixation of a calcaneus, including for example, stabilization of a fracture or reconstruction of a deformity.

BACKGROUND OF THE INVENTION

The hindfoot joint comprises the junctions formed between the cuboid, calcaneus, and the talus. Mobility in these joints is critical to almost all bipedal movement, and even standing. This joint is vulnerable to substantial damage in particular in falls, or in automobile or vehicle crashes.

The present invention is designed in a first aspect for the most common fracture to the hindfoot joint: i.e. calcaneal fractures of which the most common is a Sander's type II fracture. This type of fracture generally comprises an interior to lateral fracture which often results in a three-part fragmentation of the calcaneus often leaving the sustentaculum as the healthiest fragment and displacing laterally and posterior the remaining fragments of the calcaneus. In addition, the plate of the present invention can be used for osteotomies and fixation of other fractures or reconstruction due to trauma or deformities.

Implants have been provided in the past to try to help stabilize the fragments in order to allow the calcaneus to fuse, and these past attempts have generally provided flat plates of a somewhat flexible nature to allow a surgeon to bend the plate before implantation, and/or to allow the plate be drawn into position on the bone to allow for some contouring of the plate as part of the implantation surgery. However, the prior art plates often had elements that extended beyond the bone to irritate soft tissue such as in particular the peroneal ligaments, which often causes irritation if not eruption of the ligament. Further, while the idea of loading a flexible planar plate maybe suitable to allow contouring fixed to healthy bone, it is totally unsuitable for reconstruction or reduction of fractures so as to rebuild a fractured bone. In contrast, an aspect of the present invention provides a fully contoured plate having substantially no planar surfaces (with one small but important exception at a pre-determined origin which permits the plate to be constructed and measured). The contoured plate has a surface that faces the bone which includes radiused sections, one extending inferior to superior which is curved inferior to superior in a shape which is close to cylindrical and which approximates the shape of the cuboid bone. The second radiused section is curved in the vicinity of the anterior strut, and in particular at the inferior portion of the plate, to accommodate the peroneal tubricle.

In addition, the posterior portion or body of the plate is formed to so as to try restore maximal length and height of the calcaneus in reconstruction or reduction of the bone using the plate of the present invention. The anterior portion includes a double eared tab or tail that has upper and lower holes spaced from a central hole in the tab portion to allow for triangular multiplanar fixation. The central portion of the plate includes three fenestrations spanned by two struts extending from the inferior to the superior portions of the plate which has a contour vaguely reminiscent of the outline of a whale where the body segment beginning at the anterior strut curves through a three hole portion that is reinforced to accommodate weight transfer from the tibia to the talus to the calcaneous. The top extends from the posterior strut to the top posterior hole, and includes a translation slot which is an optional point for a surgeon to begin with fixation to the bone. This feature allows the surgeon the ability to translate the plate based on radiographic evidence once the first screw is inserted to better accommodate patient anatomy. The struts are strategically designed to maximize strength and to minimize the possibility of loss of correction through loading in use. The body generally is a blunted ovoid ring (or "whale shaped") formed of plate segments including holes for fixation screws. The posterior segment of the body extends inferiorly and slightly posteriorly to a central hole and then inferiorly and slightly anteriorly to an inferior posterior hole which has been selected as the origin for plotting of the plate, and which includes a flat counterbore from which the remainder of the plate can be plotted using Cartesian coordinates. From here, the inferior segment of the body of the plate curves slightly upward to accommodate the peroneal ligament. The plate includes holes at the inferior ends of the posterior and the anterior struts so that these struts are supported by the screws as well as the linking portions of the plate and so that the load that is taken up at the opposing ends of the struts is distributed through the struts and to the adjoining portions of the plate. The inferior hole at the anterior strut forms the end of the body of the blunted ovoid ring or "whale outline", and the tail extends anteriorly with a triangular fenestration and a superior and an inferior ear, both of which include a hole. A third hole is located in this section to maximize the number of screws that can be placed in the anterior process fragment and to allow for triangular fixation in this area. Selected fixation holes in the plate are threaded for use with locking screws. In a particular aspect of the invention there are two locking holes which are internally threaded and are designed to directly support the subtalar joint fragment, specifically just inferior to the posterior facet (i.e. the articulating surface) of the calcaneous. Optionally, the anterior portion can also include locking holes. The corresponding locking screws include mating external locking threads on the head portion. The plate further includes smaller holes which allow the use of K wires both for reduction of the fragments, and for further fixation.

In addition, the present invention provides in a separate aspect, a calcaneal plate having a reinforced portion in the vicinity of the posterior facet. This area is where the majority of the weight transfer from the tibia to the talus to calcaneus occurs. In addition the plate has a hole designed to allow placement of a screw into the sustentaculum to enable the bone to be reduced using the construct as a tool during the surgery as this is an area where subsidence is likely to occur in many fractures or breaks. Preferably the screw is a compression screw, meaning that the screw is partially rather than fully threaded and the threads are on the distil portion with a shaft area that is free from threads. In addition, the calcaneal plate provides a posterior centered superior translation slot, and support struts are provided between the inferior portion and the superior portion of the plate structure. In addition, an anterior portion has a plurality of holes to provide for the possibility to provide a choice to a surgeon who has to deal with that bone, or a bone that has been severally damaged during the trauma.

Finally, the calcaneal plate of the present invention is contoured so as to provide a construct to build the displaced/fractured bone back to, rather than contouring a plate to fit a fractured bone, which is unlikely reduced to its original disposition. Additionally, the plate is shaped to maximum the height, width and general shape that would be supported under the plate in order for a surgeon to regain the original parameters/perimeter of the calcaneus. The design is generally an organic fluid design devoid of sharp edges which in most circumstances would not project beyond the bone. Further, the design has been generalized from a survey of the population in order to provide for the best possibility of the plate being to accommodate a number of variations and individuals.

The plate is provided in a right and a left version and is generally used on the lateral portion of the calcaneal bone situated slightly posterior to the cuboid slightly inferior to the posterior facet, and supported on the posterior portion of the calcaneus. The plate is also provided in multiple profiles for small and large patients.

BRIEF DESCRIPTION OF THE DRAWINGS

The invention will be better understood and other features and advantages will become apparent by reading the detailed description of the invention, taken together with the drawings, wherein:

FIG. 1 is a top view of the plate in accordance with the invention;

FIG. 2 is a cross section of the plate of FIG. 1 taken along line 2-2;

FIG. 3 is a cross section of the plate of FIG. 1 taken along line 3-3;

FIG. 4 is a cross section of the plate of FIG. 1 taken at line 4-4;

FIG. 5 is a detail of the posterior inferior screw hole shown at 5-5;

DETAILED DESCRIPTION OF THE INVENTION

Figure 6:
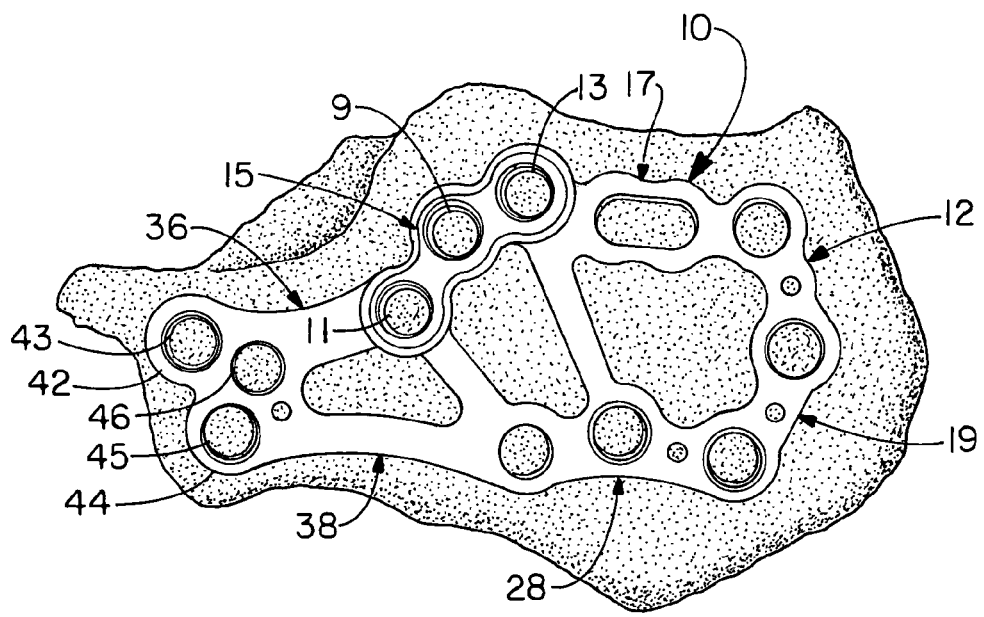
FIG. 6 is a view of the plate positioned on a calcaneal bone.

The calcaneal plate of the present invention is shown from the top in FIG. 1 at 10 and has a top outline comprising a blunt ovoid body 12 which comprises a complete ring (i.e. joined through 180°) of segments beginning at an anterior strut 14 and curving through a reinforced three hole segment (i.e., the posterior facet segment) 15 designed to fit just inferior to the posterior facet and which is reinforced by providing a greater thickness around the screw holes as well as for the areas linking the screw holes to accommodate weight transfer from the tibia to the talus to the calcaneus. The most anterior 11 and the least anterior 13 of the holes in the posterior facet segment 15 preferably are both internally threaded and receive locking screws which have corresponding mating threads on the screw head so as to lock the plate to the bone segments in this area at a pre-selected angle. The angles of the locking threads are selected to provide scaffolding for the sub-chondral support. The first locking hole 11 is at an angle of about 45° from the y-axis (in the x-y plane), 85° from the x-axis (in the x-z plane) and 5° from the z-axis (in the y-z plane) and the second locking hole 13 forms an angle of about 19° from the y-axis (in the x-y plane), 85° from the x-axis (in the x-z plane) and 15° from the z-axis (in the y-z plane). These angles are measured relative to the coordinate system established at the origin and can be varied by plus or minus about 10 degrees, preferably about 7 degrees, and most preferably about 5 degrees. The intermediate hole 9 in the posterior facet segment preferably does not include internal threads and is designed to accept a screw which is distally threaded and partially devoid of threads in order to generate compression in the bone segment and to allow the sustentaculum to be reduced using the plate. Moreover, the screw preferably also includes a blunt tip to avoid irritation of the posterior tibial nerve. This is an area of the calcaneus that is most likely in most fracture situations to have subsidence occurring.

The superior segment 17 of the body portion extends from the posterior strut 16 to the top posterior hole 22, and includes a translation slot 18 which is an optimal point for a surgeon to begin with fixation to the bone. The slot allows the surgeon to translate the plate in the anterior posterior plane to optimize placement of the particular anatomy of the patient. The plate preferably includes at least two struts, and can include additional struts. The posterior segment 19 of the body portion 12 extends inferiorly and slightly posteriorly to a central hole 24 and then inferiorly and slightly anteriorly to an inferior posterior hole 26 which has been selected as the origin for plotting of the plate, and which includes a flat counterbore 27 from which the reminder of the plate can be plotted using Cartesian coordinates. From here, the inferior segment 28 of the body portion 12 of the plate curves slightly downward and inward (i.e the plate follows an internal radius) in order to form a smooth area to avoid irritation to the peroneal ligament. The plate 10 includes holes 32, 34 at the inferior ends of the posterior and the anterior struts. The inferior hole 34 at the anterior 14 strut forms the end of the body portion, and the tail portion 36 extends anteriorly with a triangular fenestration 38 and a superior ear 42 and an inferior ear 44, each of which include a hole 43,45. The tail portion also includes a central hole 46 which allows for triangular points of fixation and as the tail portion has its own radius, the plate allows for multiplanar fixation of the anterior lateral segment close to the calcaneal cuboid joint. Optionally, various of the fixation holes within the plate are threaded with locking threads, including for example, the first and last holes of the posterior facet segment, and the holes of the tail portion. The plate further includes smaller holes 47 which allow the use of K wires both for reduction of the fragments, and for further fixation.

The plate is a fully contoured plate in all three dimensions including, notably the Z dimension and has substantially no planar surfaces, with the exception of a manufactured flat at a pre-determined origin which permits the plate to be constructed and measured. The plate has a bone facing side, wherein at least a substantial potion of this surface is intended to be in direct contact with the lateral aspect of the calcaneus, and a side which faces away from the bone, and is yet more lateral with respect to the sagittal plane. In general, the plate has a substantially uniform thickness, so that the two sides correspond in topography, with the exceptions of the posterior facet segment which includes a boss, or a raised area around the screw holes and in the areas linking the holes, and further in the area of the flat. The contoured plate includes radiused sections in the Z direction, one 52 extending inferior to superior which is curved inferior to superior in a shape which is close to cylindrical and which approximates the shape of the cuboid bone. More specifically, the bone facing side of the anterior tail portion is radiused from the inferior to the superior direction to substantially correspond to the curvature of a calcaneal cuboid joint, of which this radius is between about 5 to about 30 mm, or more preferably between about 5 and about 20 mm or about 15 mm, or most preferably equal to about 10 mm plus or minus about 2 mm. The second radiused section 54 is curved in the vicinity of the anterior strut, and in particular at the inferior portion of the plate, to accommodate the peroneal tubercle. While the topography has two distant curvatures, the areas flow into each other such that the surface of the plate undulates in a complex topography. The plate could include additional incorporated undulations, such as in the posterior to anterior direction.

Figure 7:
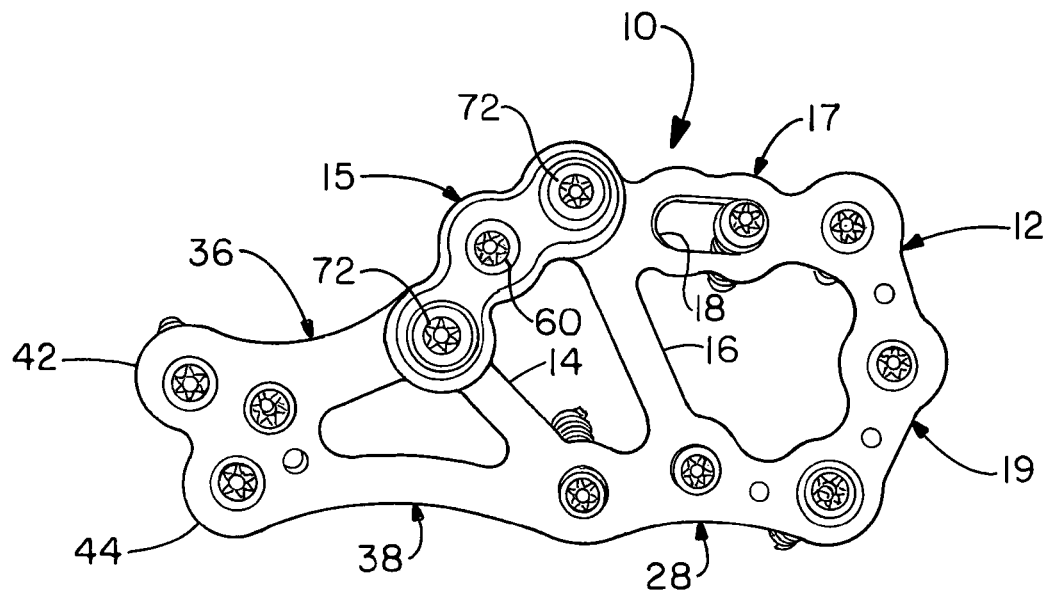
FIG. 7 is a top view of the plate including screws.
Figure 8:
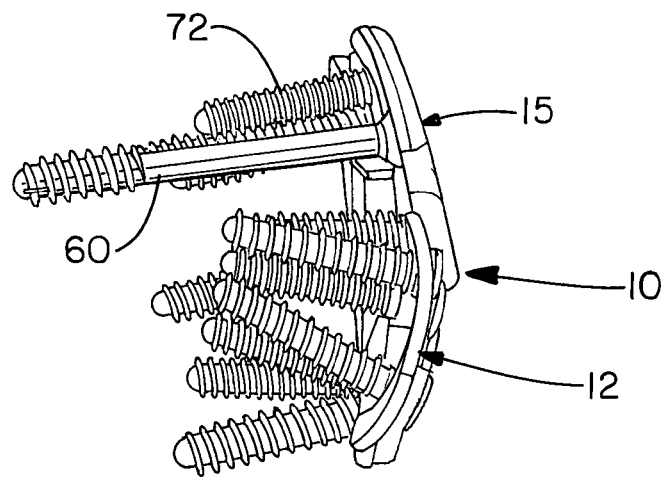
FIG. 8 is an end view of the plate including screws.

The posterior portion of the plate is formed to so as to try maximizing the length and height in reconstruction or reduction of the bone using the plate of the present invention. The anterior portion includes a double eared tab that has upper and lower holes spaced from a central hole in the tab portion. The central portion of the plate includes three fenestrations spanned by two struts extending from the inferior to the superior portions of the plate. FIGS. 7 and 8 show the plate of the present invention in two different views including a full set of screws engaging the holes of the plate.

Figure 9:
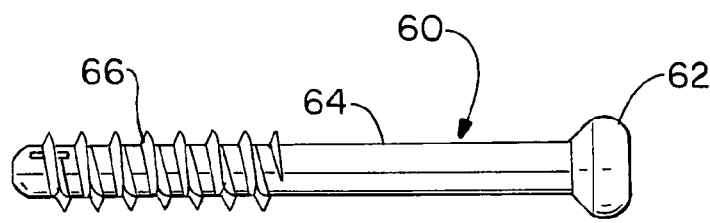
FIG. 9 is a view of the compression screw used with the plate.
Figure 10:
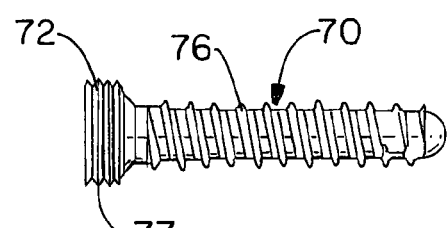
FIG. 10 is a view of a locking screw used with the plate.
Figure 11:
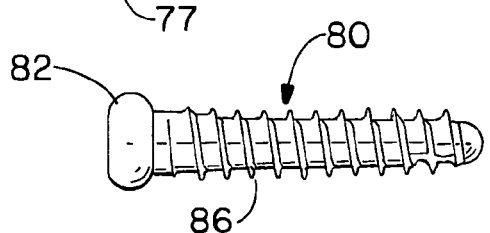
FIG. 11 is a view of a non-locking screw used with the plate.

The screws used in the construct in accordance with the present invention are shown in FIGS. 9 through 11. A compression screw 60 is shown in FIG. 9 and includes a head 62 having a rounded distal portion that seats in the screw hole in the plate at a desired angle and having a top surface with a torque driving recess. The shaft of the screw is not threaded for a first portion 64 to allow passage through a bone fragment and to capture and draw in an opposing fragment with the distally threaded portion 66. The tip is blunt to minimize soft tissue irritation at the distal end. FIG. 10 illustrates a locking screw 70 that is used in the construct. The screw 70 also includes a head 72 including a torque driving recess and having a shaft with distal threads 76. The screw includes locking threads 77 that mate with the internal threads in the locking hole to lock the plate to the bone. FIG. 11 shows a non-locking screw 80 including a head 82 having a torque driving recess and a rounded distal portion, and a shaft having cortical threads 86. The screws are provided in a variety of lengths in order to best accommodate the area of attachment of the plate.

When used in surgery, the patient is placed in a lateral decubitus position. An extensile right-angled incision is made, that begins posteriorly, just anterior to the heel cord which moves below the sural nerve and continues forward and slightly upward toward the calcaneocuboid joint. The resulting flap is elevated to expose the posterior subtalar joint. The fracture is reduced and an appropriate plate is selected since the plate of the present invention include right and left versions and further may include plates having a variety of sizes and shapes to accommodate variations in the population. The plate is placed at the appropriate position on the lateral calcaneal wall. The plate is contoured to accommodate most calcaneal surfaces, however, the plate can further be contoured by a surgeon if he or she deems it necessary. Guides wires can be inserted through the guide wire holes to hold the plate temporarily. A bicortical hole is drilled using a drill guide in the center of the translation slot and the depth of the hole is measured. The correct size non-locking screw is chosen and inserted into the slot, but not fully tightened. The position of the plate is confirmed and then the slot screw is tightened. The drill guide is used to drill a bicortical hole in the intermediate hole opening between the two threaded locking holes in the posterior facet segment. A partially threaded compression screw is inserted into this hole. A hole is drilled for the first locking screw in the posterior facet segment and a locking screw is inserted and the second locking screw is likewise inserted in the second locking hole. Screws are driven into the other holes using a similar technique until all of the holes have screws. Guide wires are removed and the incision is closed.

While in accordance with the patent statutes, the best mode and preferred embodiment have been set forth, the scope of the invention is not limited thereto, but rather by the scope of the attached claims.

What is claimed is:

1. A calcaneal plate for use on a calcaneus having a lateral aspect, the plate being fully contoured in three dimensions comprising an ovoid body portion having a superior plate segment, an anterior plate segment and an inferior plate segment, all adjacent and adjoining and defining an interior portion having at least one fenestration, the calcaneal plate including a plurality of screw holes which accept screws for attachment of the calcaneal plate to a bone, the calcaneal plate further including an anterior tail portion extending inferiorly to superiorly which has a bone facing surface that is capable of facing the calcaneus, the bone facing surface having two distinct radiuses areas which flow into one another so as to correspond to the lateral aspect of the calcaneus around its perimeter and the bone facing surface of the anterior tail portion including a curve from the inferior to the superior direction, the curve having a radius between about 5 and about 30 mm.

2. A calcaneal plate as set forth in claim 1 wherein the anterior tail portion includes a superior ear and an inferior ear.

3. A calcaneal plate as set forth in claim 2 wherein each of the superior ear and the inferior ear includes a hole for a fixation member and wherein the anterior tail portion includes a third hole to allow for triangular multiplanar fixation.

4. A calcaneal plate as set forth in claim 1 wherein one or more of the screw holes is a locking hole.

5. A calcaneal plate as set forth in claim 1 wherein the body portion has a generally uniform thickness $\delta$ and the body portion includes a posterior facet segment which has a thickness greater than $\delta$ to accommodate weight transfer from the tibia to the talus to the calcaneus.

6. A calcaneal plate as set forth in claim 5 wherein the posterior facet segment includes at least one hole for a fixation member.

7. A calcaneal plate as set forth in claim 1 wherein the body portion includes a translation slot.

8. A calcaneal plate has set forth in claim 1 further including a posterior strut and wherein the body portion includes two fenestrations with the posterior strut forming the anterior boundary of the posterior fenestration.

9. A calcaneal plate as set forth in claim 8 further including an anterior strut and the anterior strut forms the anterior boundary of the anterior fenestration.

10. A calcaneal plate as set forth in claim 9 wherein the anterior tail portion includes a triangular fenestration.

11. A calcaneal plate as set forth in claim 9 wherein there is a radiused portion of the bone facing surface in the inferior to superior direction along the anterior strut, so as to minimize irritation of the peroneal tendons.

12. A calcaneal plate as set forth in claim 1 wherein the bone facing surface has substantially no significant planar surfaces.

13. A calcaneal plate as set forth in claim 1 wherein the plate includes a posterior facet segment and the posterior facet segment includes at least two holes for fixation members.

14. A calcaneal plate as set forth in claim 13 wherein at least one of the posterior facet holes is a locking hole.

15. A calcaneal plate as set forth in claim 13 wherein at least two of the holes of the posterior facet segment are threaded holes each of which defines an axis which forms an angle relative to a Cartesian coordinate system which has been defined for the plate, and in which the angle of the threaded holes are capable of forming a scaffold for a subchondral support.

16. A calcaneal plate as set forth in claim 15 wherein the posterior facet segment includes at least three holes.

17. A calcaneal plate as set forth in claim 16 wherein the plate has a thickness in the Z direction and the posterior facet segment includes holes and areas linking the holes and the plate surrounding the holes and linking the holes has an increased thickness in the Z direction relative to the thickness of the plate.

18. A calcaneal plate as set forth in claim 16 wherein one of the holes of the posterior facet segment does not include internal threads.

19. A calcaneal plate as set forth in claim 17 further including a compression screw and wherein the one of the holes of the posterior facet segment which does not include threads accepts a compression screw.

20. A calcaneal plate as set forth in claim 1 wherein the plate further includes an anterior tail portion and wherein the anterior tail segment portion in an anterior posterior direction and which includes three holes that provide for triangular multi planar fixation.

21. A calcaneal plate as set forth in claim 1 wherein at least one of the radiused areas curves in the direction anterior to posterior relative to a lateral aspect of a calcaneus.

22. A calcaneal plate as set forth in claim 1 wherein at least one of the radiused areas curves in the direction inferior to superior relative to a lateral aspect of a calcaneus.

23. A calcaneal plate as set forth in claim 1 wherein at least one of the radiused areas curves in the direction anterior to posterior relative to a lateral aspect of a calcaneus and the other is in the direction inferior to superior relative to the lateral aspect of a calcaneus.

24. A calcaneal plate as set forth in claim 1 which is capable of being implanted on a posterior facet of an ankle joint having an axis of loading, the plate having a posterior facet portion which is contoured for placement in the vicinity of the posterior facet and providing support along the axis of loading of the ankle joint and including at least one threaded hole inferior to the posterior facet to inhibit subsidence of an affected bone fragment after implantation of the plate.

25. A calcaneal plate as set forth in claim 24 wherein the posterior facet portion includes at least two threaded holes.

26. A calcaneal plate as set forth in claim 24 wherein the posterior facet portion includes at least one non-threaded hole.

27. A calcaneal plate as set forth in claim 26 wherein the non-threaded hole receives a partially threaded screw.

28. A calcaneal plate as set forth in claim 1 which is for use in Sander' type II, III & IV fractures having an anterior portion that includes three holes for fixation of an anterior process fragment.

29. A calcaneal plate as set forth in claim 28 further including a compression screw and wherein at least one of the holes receives the compression screw.

* * * * *